(12) United States Patent
Lee et al.

(10) Patent No.: US 9,791,630 B2
(45) Date of Patent: Oct. 17, 2017

(54) APPARATUS FOR DISCRIMINATING BACTERIA TYPES USING OPTICAL SCATTERING PATTERNS

(71) Applicant: Pukyong National University Industry-University Cooperation Foundation, Busan (KR)

(72) Inventors: Yongwook Lee, Busan (KR); Junghwan Oh, Busan (KR); Hyunwook Kang, Busan (KR); Seungyun Nam, Busan (KR); Youngmog Kim, Busan (KR); Junhyeog Jeong, Busan (KR)

(73) Assignee: Pukyong National University Industry-University Cooperation Foundation, Busan (KR)

( * ) Notice: Subject to any disclaimer, the term of this patent is extended or adjusted under 35 U.S.C. 154(b) by 0 days.

(21) Appl. No.: 15/224,675

(22) Filed: Aug. 1, 2016

(65) Prior Publication Data

US 2017/0038289 A1 Feb. 9, 2017

(30) Foreign Application Priority Data

Aug. 3, 2015 (KR) ........................ 10-2015-0109317

(51) Int. Cl.
| | |
|---|---|
| *G01N 21/00* | (2006.01) |
| *G02B 6/32* | (2006.01) |
| *G02B 6/27* | (2006.01) |
| *G01N 15/06* | (2006.01) |
| *C12M 1/34* | (2006.01) |
| *G01N 15/00* | (2006.01) |

(52) U.S. Cl.
CPC ............. *G02B 6/32* (2013.01); *C12M 1/3453* (2013.01); *G01N 15/06* (2013.01); *G02B 6/2706* (2013.01); *G01N 2015/0065* (2013.01)

(58) Field of Classification Search
CPC ........... G01N 15/1429; G01N 15/1434; G02B 6/2706; G02B 6/32
USPC ....................................................... 356/338
See application file for complete search history.

(56) References Cited

U.S. PATENT DOCUMENTS

| | | | | |
|---|---|---|---|---|
| 5,667,656 | A | * | 9/1997 | Kambara ......... G01N 27/44721 204/603 |
| 2003/0082516 | A1 | * | 5/2003 | Straus .............. G01N 33/56916 435/4 |

(Continued)

FOREIGN PATENT DOCUMENTS

KR 10-1237368 B1 3/2013

OTHER PUBLICATIONS

Agnieszka Suchwalko et al., "Bacteria species identification by the statistical analysis of bacterial colonies Fresnel patterns", Optics Express, May 6, 2013, pp. 11322-11337, vol. 21, No. 9.

*Primary Examiner* — Sunghee Y Gray
(74) *Attorney, Agent, or Firm* — Revolution IP, PLLC

(57) ABSTRACT

An apparatus for discriminating bacteria types using optical scattering patterns is disclosed. The apparatus includes an optical fiber for transferring light emitted from a light source, a lens for controlling a width of the light received from the optical fiber, a linear polarizer for transmitting the light passing through the lens and a bacterial colony, and a capturing unit for capturing an optical scattering pattern of the light transmitted through the linear polarizer.

5 Claims, 5 Drawing Sheets

(56) References Cited

U.S. PATENT DOCUMENTS

| | | | |
|---|---|---|---|
| 2006/0172370 A1* | 8/2006 | Hirleman, Jr. | G01N 21/21 435/34 |
| 2007/0058252 A1* | 3/2007 | Fritz | G01N 15/1404 359/485.05 |
| 2008/0058629 A1* | 3/2008 | Seibel | A61B 1/0008 600/368 |
| 2012/0010513 A1* | 1/2012 | Wong | A61B 1/00165 600/476 |
| 2012/0076493 A1* | 3/2012 | Zhang | H04B 10/2569 398/29 |
| 2015/0054921 A1* | 2/2015 | Dixon | G02B 21/26 348/46 |
| 2015/0285728 A1* | 10/2015 | Ozdemir | G01N 15/1434 356/301 |

* cited by examiner (a)

(b)

(a)          (b)

APPARATUS FOR DISCRIMINATING BACTERIA TYPES USING OPTICAL SCATTERING PATTERNS

This application claims the benefit of Korean Patent Application No. 2015-0109317, filed on Aug. 3, 2015, which is hereby incorporated by reference as if fully set forth herein.

BACKGROUND

Field of the Invention

The present invention relates to an apparatus for discriminating the species of unknown bacteria rapidly with high accuracy, using an optical scattering pattern, and more particularly, to an apparatus for acquiring an optical scattering pattern to which polarization interference has occurred, using a single polarizer and a single polarization controller, and discriminating a bacterial species using the optical scattering pattern.

Discussion of the Related Art

Bacteria are everywhere, such as in food, animals, and human beings. If a human is infected with bacteria, he or she may suffer from fever, sickness, blood poisoning, food poisoning, and the like. Among them, *Escherichia coli* is commonly found in the lower intestine of humans or animals and may be discharged out in excretion, or during slaughter of animals. *Escherichia coli* is generally normal in the colon. However, *Escherichia coli* may cause peritonitis, blood poisoning, and so on in parts other than the colon. Even in the colon, pathogenetic *Escherichia coli* may cause infectious diarrhea. *Listeria* grows well in fast food, dairy food, and meat and causes blood poisoning and meningitis. Its death rate reaches 20 to 25%. *Salmonella* grows well even at low temperature, and its main infection source is poultry and eggs. If a human is infected with *salmonella, salmonella* may cause typhoid with diarrhea, fever, or stomachache, coloenteritis, and the like.

These bacteria may adversely affect economy as well as health. If the number of bacteria in various foods, materials, and water exceeds a reference value, all of the items should be withdrawn, thus causing economic loss.

Therefore, bacterial detection and discrimination is significant for human health and economy.

Conventionally, an immune analysis scheme using an antibody, a DNA-based molecular biological scheme, a luminous principle-based analysis scheme, an electric resistance analysis scheme, an optical scattering pattern detection scheme, and so on are available for bacterial detection and discrimination.

Among them, the optical scattering pattern detection scheme uses an optical scattering pattern obtained by transmitting light from a laser diode through two linear polarizers and a bacterial colony in an open free space.

A shortcoming with the conventional optical scattering pattern detection scheme is that each time a new scattering pattern is to be acquired for the same bacterial colony, a test device should be reset because the laser diode is arranged in a light-shielding capturing unit.

Moreover, since light from the laser diode is immediately guided to the open free space, light is easily introduced from the outside in the conventional optical scattering pattern detection scheme. The resulting influence on a final detected scattering pattern makes it difficult to obtain a clear scattering pattern unique to the bacterial colony.

SUMMARY

Accordingly, the present invention is directed to an apparatus for discriminating bacteria types using optical scattering patterns that substantially obviates one or more problems due to limitations and disadvantages of the related art.

An object of the present invention is to provide an apparatus for enabling free arrangement of a laser diode during capturing of an optical scattering pattern, acquiring various clear optical scattering patterns for one bacterial colony by easily controlling the polarization of light emitted from the laser diode, and discriminating a bacterial species easily and accurately, using the optical scattering patterns.

To achieve these objects and other advantages and in accordance with the purpose of the invention, as embodied and broadly described herein, an apparatus for discriminating bacteria types using optical scattering patterns includes an optical fiber for transferring light emitted from a light source, a lens for controlling a width of the light received from the optical fiber, a linear polarizer for transmitting the light passing through the lens and a bacterial colony, and a capturing unit for capturing an optical scattering pattern of the light transmitted through the linear polarizer. A polarization controller may be provided at the optical fiber, for polarizing the light guided through the optical fiber.

The apparatus may further include an x-y axis stage for disposing the bacterial colony thereon, and controlling a horizontal position of the disposed bacterial colony.

The apparatus may further include a z axis stage combined with the capturing unit, for controlling a vertical distance between the capturing unit and the bacterial colony.

The width of the light passing through the lens may be controlled to 100 µm to 1 mm.

The polarization controller may include a ½ wavelength plate or a ¼ wavelength plate.

It is to be understood that both the foregoing general description and the following detailed description of the present invention are exemplary and explanatory and are intended to provide further explanation of the invention as claimed.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION

Figure 1:
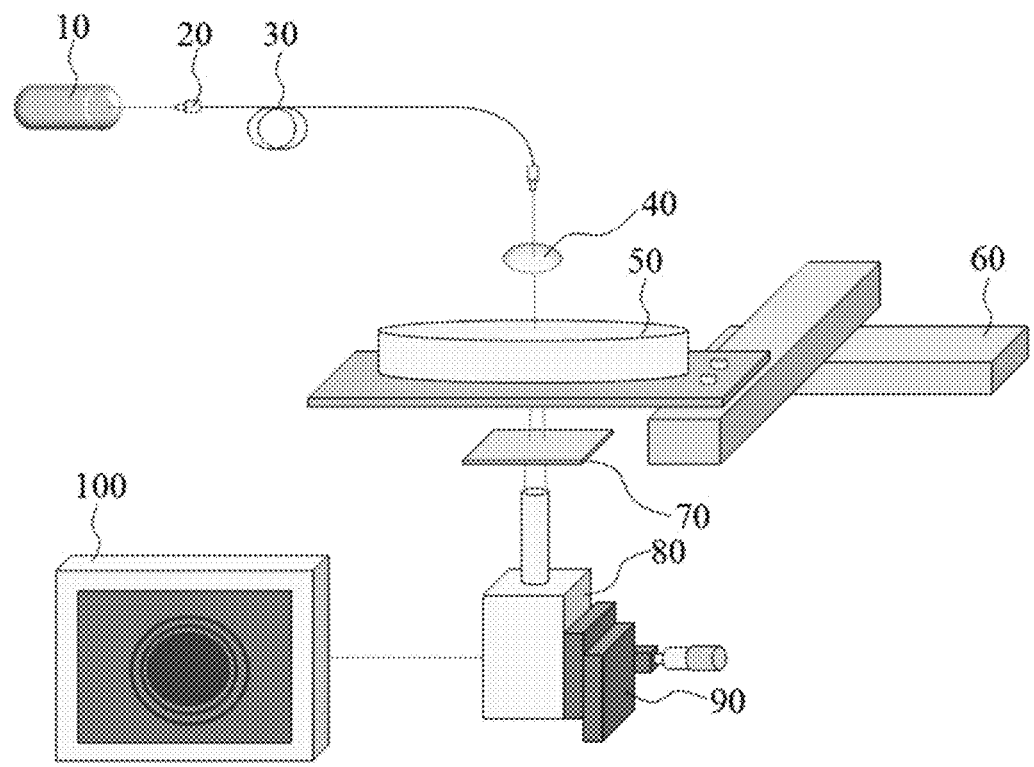
FIG. 1 is a schematic view of an apparatus for discriminating a bacterial species, using an optical scattering pattern according to a preferred embodiment of the present invention.

With reference to the attached drawings, a preferred embodiment of the present invention will be described in detail. Like reference numerals denote the same or corresponding components in the drawings. Further, a description of technical contents which are known to the field of the present invention and have no direct relation to the present invention is omitted in the following description of the embodiment, lest it should not obscure the subject matter of the present invention. While the preferred embodiment of the present invention will be described below, it is to be clearly understood that the present invention is not limited thereto and can be implemented by those skilled in the art.

FIG. 1 is a schematic view of an apparatus for identifying a bacterial species, using an optical scattering pattern according to a preferred embodiment of the present invention.

With reference to FIG. 1, an apparatus 1 for discriminating a bacterial species, using an optical scattering pattern according to a preferred embodiment of the present invention will be described.

The apparatus 1 for discriminating a bacterial species, using an optical scattering pattern according to the preferred embodiment of the present invention includes a light source 10, an optical fiber 20, a polarization controller 30, a lens 40, a Petri dish 50, an x-y axis stage 60, a linear polarizer 70, a capturing unit 80, a z axis stage 90, and an output unit 100.

Specifically, the light source 10 may include a laser diode that outputs light in a wavelength range of visible rays.

Preferably, light output from the light source 10 is a laser beam, that is, a 532-nm visible laser beam.

The optical fiber 20 receives the light emitted from the light source and transfers the received light to the lens 40. Since a laser beam emitted from a laser diode is linear, the laser diode should be arranged over the Petri dish 50 in a straight line to a bacterial colony contained in the Petri dish 50. In a structure of emitting a beam from a light source through an optical fiber according to an embodiment of the present invention, the optical fiber 20 is bendable and thus light may be projected onto the Petri dish 50 even though the light source 10 is not placed over the Petri dish 50. That is, as illustrated in FIG. 1, even though the optical fiber 20 is positioned at a side of the Petri dish 50, as far as the optical fiber 20 is bent so that an end of the optical fiber 20 is arranged in a straight line to the Petri dish 50, a beam may be transferred from the light source 10. Accordingly, since the light source 10 may be disposed very freely, the bacteria identifying apparatus 1 may be scaled down in volume and thus miniaturized. Also, the use of an optical fiber may facilitate access of light to a bacterial colony.

Depending on its mode, the optical fiber 20 may be one of a single-mode fiber, a multi-mode step index fiber, a multi-mode graded index fiber, and a large-diameter multi-mode fiber.

If a single-mode fiber having a conical, pyramid, or semi-spherical longitudinal section, that is, a lensed fiber is used as the optical fiber 20, a lens effect may be achieved and thus the diameter of an output beam may be reduced to or below 10 μm. As the beam diameter is decreased, an optical scattering pattern for a small-size (tens of μm) bacterial colony may advantageously be obtained without light diffraction.

Figure 6:
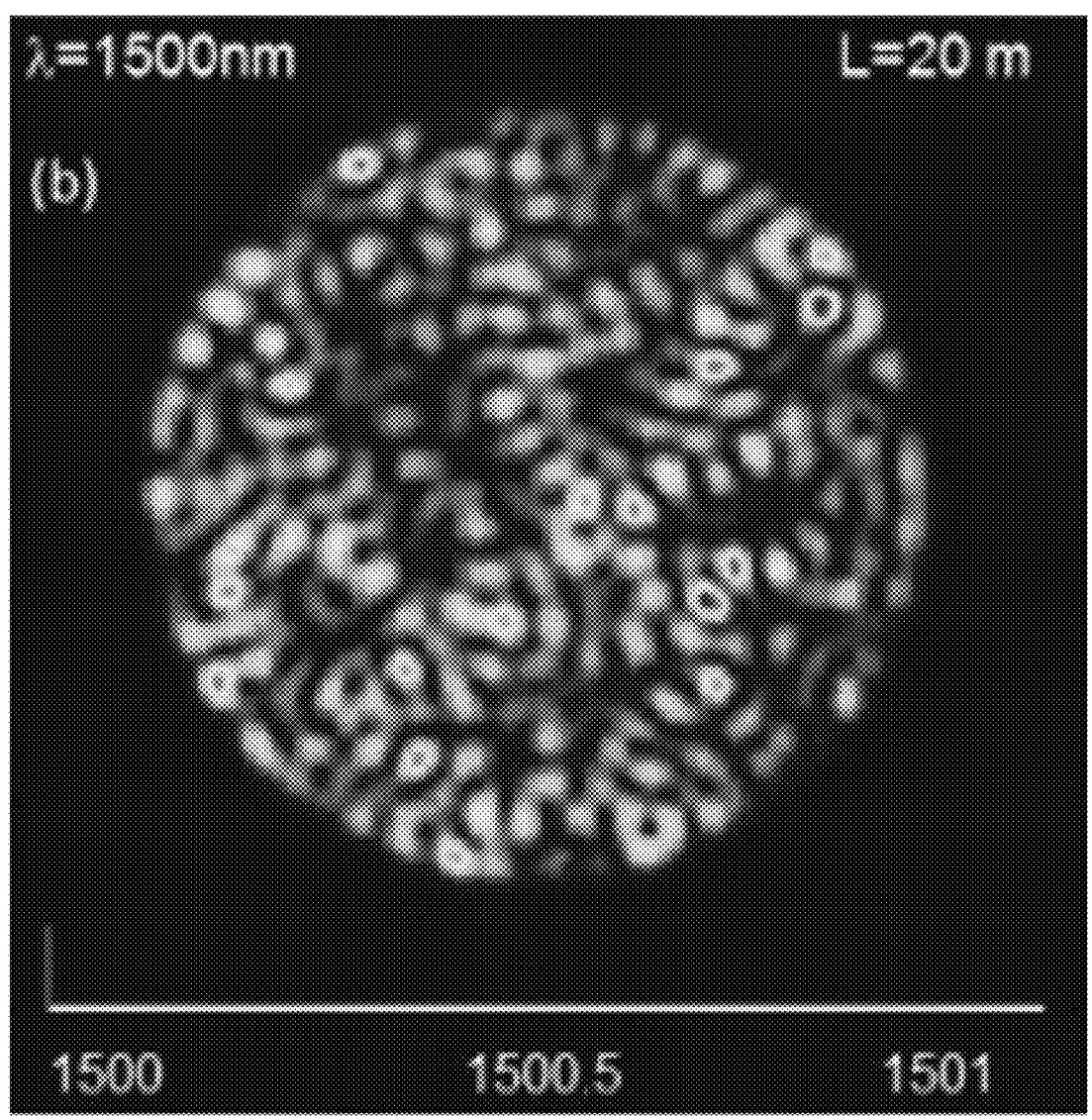
FIG. 6 illustrates an image of a speckle pattern.

On the other hand, if a multi-mode fiber with a core diameter of 50 to 60 μm is used as the optical fiber 20, a speckle pattern may be generated from an output beam, as illustrated in FIG. 6. If a beam producing a speckle pattern having a complex wave front instead of plane waves is used, a new optical scattering pattern may be obtained, thereby increasing the probability of bacteria discrimination. Depending on its material, the optical fiber 20 may be one of a silica-based fiber, a fluoride-based fiber, a rare earth-doped fiber, a polymer-based fiber, and a lead glass optical fiber.

Besides, the optical fiber 20 may be one of a polarization-maintaining fiber, a non-linear fiber, a dispersion-shifted fiber, a dispersion-compensating fiber, and a non-zero dispersion-shifted fiber.

The polarization controller 30 is provided at the optical fiber 20, to polarize light emitted from the light source 10 and guided through the optical fiber 20.

The polarization controller 30 may be configured by connecting a ½ wavelength plate or a ¼ wavelength plate to a U-shaped bracket.

Since there is no need for positioning the light source 10, the optical fiber 20, and the polarization controller 30 in the vicinity of a capturing area in which the lens 40, the linear polarizer 70, and the capturing unit 80 are arranged, the light source 10, the optical fiber 20, and the polarization controller 30 may be arranged relatively freely.

When an optical scattering pattern of a bacterial colony is captured, the capturing unit should be maintained shielded from external light. If light is projected into the capturing area through an end tip of the optical fiber 20 and the polarization controller 30 is disposed outside the capturing area, polarization may be controlled easily without changing the state of the capturing area even during capturing of an optical scattering pattern.

In the course of guiding light emitted from the light source 10 along the optical fiber 20, light loss occurs. However, the light loss does not matter because a low light intensity is required in obtaining an optical scattering pattern of a bacterial colony to prevent damage to the bacterial colony and the capturing unit 80.

In general, the light intensity is about 50 μW in a test for obtaining an optical scattering pattern of a bacterial colony. Fine control of the light intensity may be performed by controlling current of the light source 10 to 0 to 2.5 A. After the light with the controlled light intensity is guided through the optical fiber 20, the polarization of the light may be controlled arbitrarily by means of the polarization controller 30.

The lens 40 functions to control the width of the light projected from the optical fiber 20 after the light is polarized by the polarization controller 30.

The lens 40 may be a bi-convex lens and control the width of light preferably to 100 μm to 1 mm according to the size of a bacterial colony.

The reason for controlling the light width is that a clear, accurate scattering pattern may be obtained when the size of the bacterial colony matches the light width, and light is scattered by the internal structure of the bacterial colony during projection of light controlled according to the size of the bacterial colony onto the center of the bacterial colony.

The bacterial colony is accommodated in a transparent test vessel which allows light transmission, such as the Petri dish 50.

To acquire a clear optical scattering pattern of the bacterial colony, the center of light projected from the light source 10 should be aligned with the center of the bacterial colony. For alignment between the center of the light and the center of the bacterial colony, the x-y axis stage 60 is provided.

The Petri dish 50 containing the bacterial colony is placed on the x-y axis stage 60, and the horizontal position of the bacterial colony is adjusted by the x-y axis stage 60. Preferably, the x-y axis stage 60 is configured to adjust the horizontal position with precision in units of micrometer by connecting a control module to a computer.

The linear polarizer 70 is disposed at the rear end of the lens 40. The light transmitted through the lens 40 and then the center of the bacterial colony at the position adjusted by the x-y axis stage 60 passes through the linear polarizer 70.

Since the bacterial colony contains a double refraction component, the polarization of the light transmitted through the bacterial colony is partially different. Double refraction means different refraction indexes for polarization. Light with polarization changed at the double refraction component passes through the linear polarizer 70, thus producing a polarization-interference optical scattering pattern.

The polarization interference results in a change in the spatial light power of an optical scattering pattern.

If polarization is controlled by changing an azimuth angle of the polarization controller 30, different polarization results due to the double refraction component of the bacterial colony. The resulting different polarization interference leads to a different change in the light power of an optical scattering pattern. In this manner, various optical scattering patterns may be acquired from one bacterial colony, and a bacterial species may be identified fast and accurately, using the optical scattering patterns.

The capturing unit 80 captures a scattering pattern of light that has passed through the linear polarizer 70. The capturing unit 80 may be configured as an image capturing device such as a Charge-Coupled Device (CCD) camera.

The capturing unit 80 may be combined with the z axis stage 90, and control a vertical distance to the bacterial colony.

The z axis stage 90 may be configured to be manipulated manually, or electronically by a computer, like the z-y axis stage 60.

Image information about an optical scattering pattern of the bacterial colony captured by the capturing unit 80 may be transmitted to the output unit 100 configured as a Liquid Crystal Display (LCD) monitor or the like, so that an observer may view the optical scattering pattern.

Figure 2:
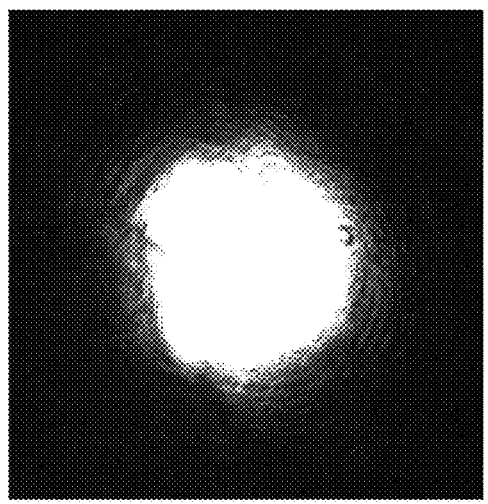
FIG. 2 illustrates scattering patterns captured before and after light emitted from a light source passes through a bacterial colony.
Figure 2:
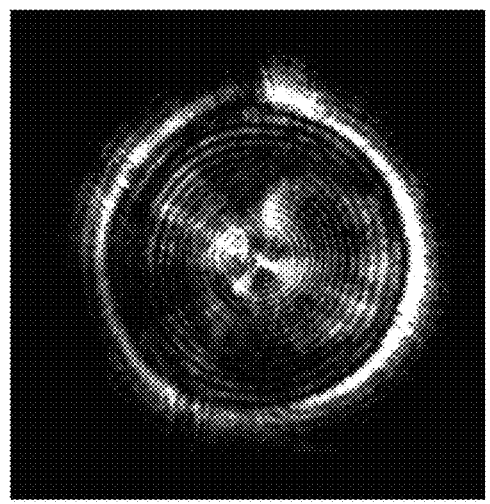

FIG. 2 illustrates scattering patterns captured before and after light emitted from a light source passes through a bacterial colony.

Specifically, (a) of FIG. 2 illustrates an image captured after a 532-nm visible laser beam passes through a part without a bacterial colony in the Petri dish 50 containing a bacterial colony, and (b) of FIG. 2 illustrates an image captured after the 532-nm visible laser beam passes through the bacterial colony.

A comparison between (a) and (b) of FIG. 2 reveals that a simple circular light produces a unique scattering pattern by passing through the bacterial colony.

Figure 3:
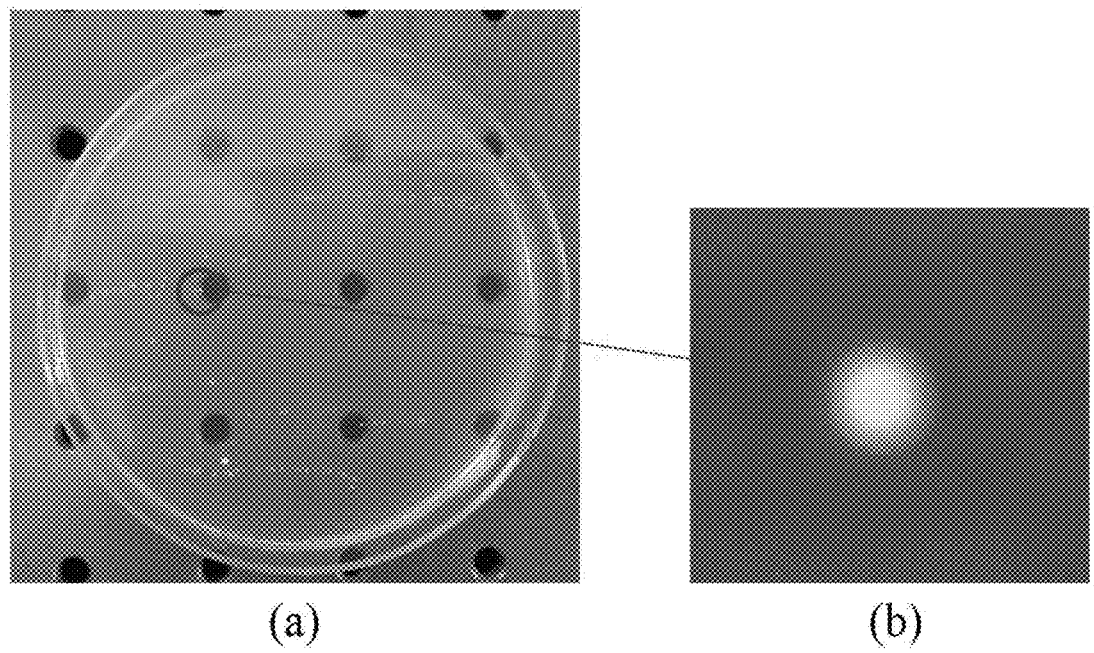
FIG. 3 illustrates a captured image of all of bacterial colonies cultured in a streak plate method, and a captured enlarged image of one bacterial colony.

FIG. 3 illustrates a captured image of all of bacterial colonies cultured in a streak plate method, and a captured enlarged image of one bacterial colony.

Specifically, (a) of FIG. 3 illustrates an image of the whole Petri dish 50 containing bacterial colonies. In (a) of FIG. 3, white spots represent the bacterial colonies, and the yellow background around the white spots represents a culture medium. FIG. 3(*b*) is an enlarged view of one bacterial colony of a size equal to or smaller than 257 μm, which has been cultured in the culture medium for 24 hours.

The size of a bacterial colony may be controlled by controlling the culture time of bacteria in the culture medium. As the culture time increases, the size of the bacterial colony also increases.

Figure 4:
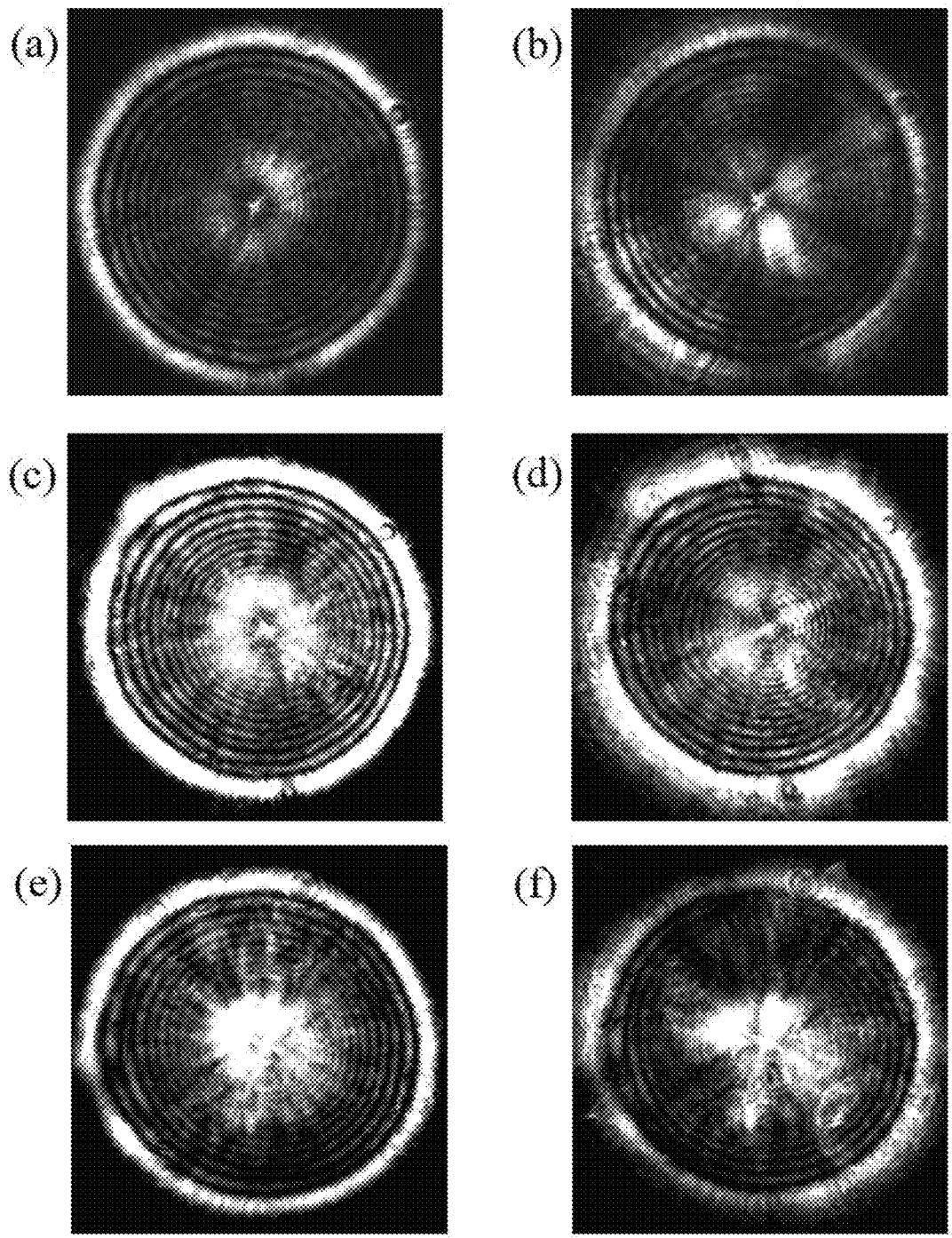
FIG. 4 illustrates scattering patterns of three bacterial colonies, with (a), (c), and (e) being images of the bacterial colonies captured without a linear polarizer, and (b), (d), and (f) being images of the bacterial colonies captured with a linear polarizer.

FIG. 4 illustrates scattering patterns of three bacterial colonies, with (a), (c), and (e) being images of the bacterial colonies captured without a linear polarizer, and (b), (d), and (f) being images of the bacterial colonies captured with a linear polarizer installed.

Each pair of (a) and (b), (c) and (d), and (e) and (f) is captured images of the same bacterial colony.

The optical scattering patterns (a), (c), and (e) of the bacterial colonies produced without the linear polarizer 70 are shown as multiple simple concentric circles on the whole, whereas different light intensities are observed partially and clover patterns with crossing light and dark areas are shown especially at the centers of the optical scattering patterns (b), (d), and (f) of the bacterial colonies produced with the linear polarizer 70.

The clover patterns at the centers of the optical scattering patterns (b), (d), and (f) may be acquired when the optical scattering patterns are captured with a light intensity and a light size which are appropriately set and with alignment between the center of light and the center of a bacterial colony. A scattering pattern having different characteristics from those of a conventional scattering pattern may be obtained by controlling polarization in the above manner.

Figure 5:
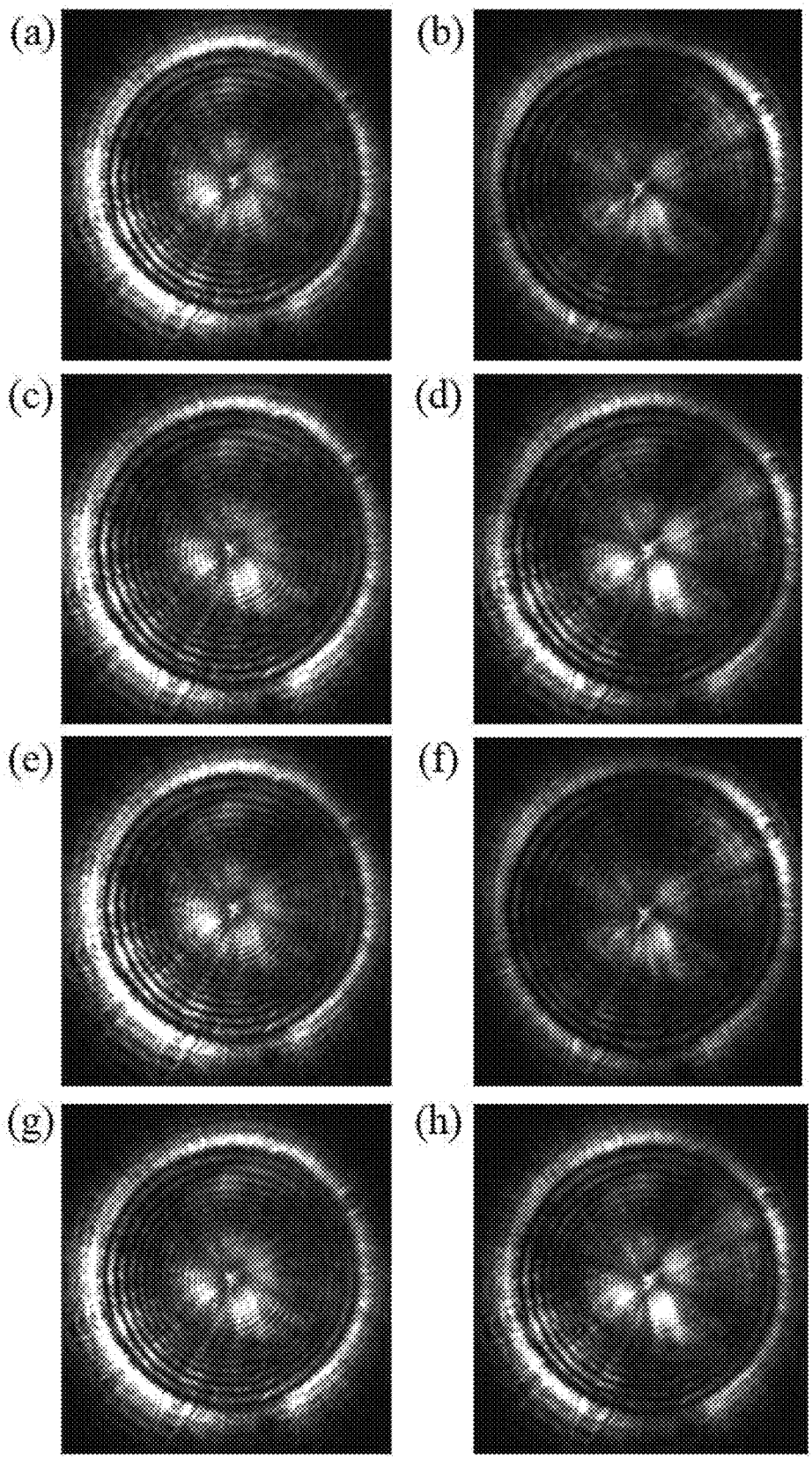
FIG. 5 illustrates scattering patterns of one bacteria colony, with (a)-(h) being images captured with polarization controlled to azimuth angles of 0°, 45°, 90°, 135°, 180°, 225°, 270°, and 315° for one bacterial colony, respectively.

FIG. 5 illustrates scattering patterns of one bacteria colony, with (a)-(h) being images captured with polarization controlled to azimuth angles of 0°, 45°, 90°, 135°, 180°, 225°, 270°, and 315° for one bacterial colony, respectively.

Referring to FIG. 5, it may be noted from the images that polarization varies with control of an azimuth angle and thus a light area and a dark area are changed greatly.

Each pair of (a) and (e), (b) and (f), (c) and (g), and (d) and (h) has a 180° azimuth angle difference. The resulting same double refection results in similar scattering patterns.

As is apparent from the foregoing description, the apparatus 1 for identifying a bacterial species, using an optical scattering pattern according to the present invention enables securing of a plurality of optical scattering patterns which vary according to polarization for a single bacterial colony, and can fast and accurately identify a bacterial species, using the secured optical scattering patterns. Therefore, the apparatus 1 is very useful in identifying a bacterial species using an optical scattering pattern.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. An apparatus for discriminating bacteria types using optical scattering patterns, the apparatus comprising:

an optical fiber transferring light emitted from a light source;

a polarization controller being disposed at the optical fiber and configured to change polarization of the light emitted from the light source along the optical fiber by adjusting an azimuth angle of the polarization controller so that a variety of optical scattering patterns is acquired from a single bacterial colony;

a lens controlling a width of the light received from the optical fiber;

a linear polarizer transmitting the light passing through the lens and the single bacterial colony; and a capturing unit capturing an optical scattering pattern of the light transmitted through the linear polarizer, wherein the lens, the linear polarizer, and the capturing unit are included in a capturing area, which is maintained shielded from external light, wherein the light source, the optical fiber, and the polarization controller are movably arranged outside the capturing area.

2. The apparatus according to claim 1, further comprising an x-y axis stage disposing the single bacterial colony thereon, and controlling a horizontal position of the disposed bacterial colony.

3. The apparatus according to claim 1, further comprising a z axis stage combined with the capturing unit, controlling a vertical distance between the capturing unit and the single bacterial colony.

4. The apparatus according to claim 1, wherein the width of the light passing through the lens is controlled to 100 μm to 1 mm.

5. The apparatus according to claim 2, wherein the polarization controller includes a ½ wavelength plate or a ¼ wavelength plate.

* * * * *